United States Patent
Furukawa et al.

(10) Patent No.: US 11,932,762 B2
(45) Date of Patent: Mar. 19, 2024

(54) ADHESIVE FOR ENDOSCOPE, CURED PRODUCT, ENDOSCOPE, AND METHOD FOR PRODUCING ENDOSCOPE

(71) Applicant: FUJIFILM Corporation, Tokyo (JP)

(72) Inventors: Kazushi Furukawa, Kanagawa (JP); Yoshihiro Nakai, Kanagawa (JP); Shigeki Uehira, Kanagawa (JP)

(73) Assignee: FUJIFILM Corporation, Tokyo (JP)

(*) Notice: Subject to any disclaimer, the term of this patent is extended or adjusted under 35 U.S.C. 154(b) by 909 days.

(21) Appl. No.: 16/936,825

(22) Filed: Jul. 23, 2020

(65) Prior Publication Data

US 2021/0007579 A1 Jan. 14, 2021

Related U.S. Application Data (63) Continuation of application No. PCT/JP2019/005584, filed on Feb. 15, 2019.

(30) Foreign Application Priority Data

Feb. 27, 2018 (JP) .................. 2018-033848

(51) Int. Cl.

| | |
|---|---|
| *C08L 75/04* | (2006.01) |
| *A61B 1/00* | (2006.01) |
| *A61B 1/005* | (2006.01) |
| *C09J 5/00* | (2006.01) |
| *C09J 11/06* | (2006.01) |
| *C09J 163/00* | (2006.01) |
| *C09J 163/08* | (2006.01) |
| *A61B 1/05* | (2006.01) |

(52) U.S. Cl.
CPC ............ *C08L 75/04* (2013.01); *A61B 1/0011* (2013.01); *A61B 1/005* (2013.01); *C09J 5/00* (2013.01); *C09J 11/06* (2013.01); *C09J 163/00* (2013.01); *C09J 163/08* (2013.01); A61B 1/00096 (2013.01); A61B 1/051 (2013.01); C09J 2463/00 (2013.01)

(58) Field of Classification Search
USPC ....................................................... 528/393
See application file for complete search history.

(56) References Cited

U.S. PATENT DOCUMENTS

| | | | | |
|---|---|---|---|---|
| 4,726,868 | A * | 2/1988 | Goel | ................ C09J 175/04 |
| | | | | 156/330 |
| 9,828,534 | B2 * | 11/2017 | Renkel | ................ B29C 70/48 |
| 2006/0036130 | A1 * | 2/2006 | Fitzpatrick | .............. A61B 1/018 |
| | | | | 600/920 |
| 2010/0279491 | A1 | 11/2010 | Kiuchi et al. | |
| 2011/0245614 | A1 | 10/2011 | Nakamura | |
| 2012/0082842 | A1 | 4/2012 | Hirano et al. | |
| 2014/0037966 | A1 | 2/2014 | Renkel et al. | |
| 2014/0128669 | A1 | 5/2014 | Kobayashi et al. | |
| 2014/0274720 | A1 | 9/2014 | Kims et al. | |
| 2015/0240137 | A1 | 8/2015 | Yokoyama et al. | |
| 2016/0222261 | A1 * | 8/2016 | Yokoyama | ............... B32B 7/12 |
| 2017/0035277 | A1 * | 2/2017 | Kucharski | .............. A61B 1/018 |
| 2019/0082937 | A1 | 3/2019 | Hayashi et al. | |

FOREIGN PATENT DOCUMENTS

| | | |
|---|---|---|
| CN | 102471661 A | 5/2012 |
| CN | 103703096 A | 4/2014 |
| CN | 104781364 A | 7/2015 |
| EP | 0399311 A2 * | 11/1990 ............ C09J 175/04 |
| EP | 1847213 A1 | 10/2007 |
| EP | 3281965 A1 | 2/2018 |
| JP | 2005-152461 A | 6/2005 |
| JP | 2011-110116 A | 6/2011 |
| JP | 2013-118281 A | 6/2013 |
| JP | 2015-63595 A | 4/2015 |
| JP | 2017-214546 A | 12/2017 |
| WO | WO-0140396 A2 * | 6/2001 ............ C08G 18/10 |

OTHER PUBLICATIONS

EP0399311 see machine translation (Year: 1990).*
Communication dated Mar. 1, 2021, from the European Patent Office in European Application No. 19761254.2.
Office Action dated Mar. 1, 2023, issued in corresponding Chinese Application No. 201980011199.9.
International Search Report dated Apr. 16, 2019 in International Application No. PCT/JP2019/005584.
International Preliminary Report on Patentability dated Dec. 20, 2019 in International Application No. PCT/JP2019/005584.

* cited by examiner

*Primary Examiner* — Terressa Boykin
(74) *Attorney, Agent, or Firm* — Sughrue Mion, PLLC (57) ABSTRACT

A two-component adhesive for an endoscope and a cured product thereof, the adhesive having a base resin and a curing agent. The base resin contains an epoxy resin (A), and the epoxy resin (A) includes an epoxy resin (a) having an average degree of polymerization of 2 or more. Also disclosed are an endoscope produced by using the adhesive for an endoscope and a method for producing the endoscope.

12 Claims, 3 Drawing Sheets

ADHESIVE FOR ENDOSCOPE, CURED PRODUCT, ENDOSCOPE, AND METHOD FOR PRODUCING ENDOSCOPE

CROSS-REFERENCE TO RELATED APPLICATIONS

This application is a Continuation of PCT International Application No. PCT/JP2019/005584 filed on Feb. 15, 2019, which claims priority under 35 U.S.C. § 119 (a) to Japanese Patent Application No. 2018-033848 filed in Japan on Feb. 27, 2018. Each of the above applications is hereby expressly incorporated by reference, in its entirety, into the present application.

BACKGROUND OF THE INVENTION

1. Field of the Invention

The present invention relates to an adhesive for an endoscope, a cured product, an endoscope, and a method for producing an endoscope.

2. Description of the Related Art

An insertion section of an endoscope is inserted into a body cavity through the oral cavity or nasal cavity. To alleviate foreign body sensation and pain in patients during the insertion, the insertion section of an endoscope desirably has a smaller diameter. Thus, instead of bulky members such as screws, adhesives are mainly used to bond together members constituting the insertion section.

A flexible tube constituting the insertion section of an endoscope needs to be washed and disinfected with chemicals after each use. To prevent infectious diseases, high cleanliness at the level of sterilization higher than disinfection is required particularly when an endoscope is inserted into a highly susceptible region such as a bronchus. Recently, in addition to ethylene oxide gas (EOG) sterilization treatment, which is widely practiced, treatments having higher sterilization effects, for example, with hydrogen peroxide plasma have also been desired. Accordingly, adhesives applied to endoscopes are required to be able to maintain their adhesiveness after repetition of these sterilization treatments.

Among the adhesives, epoxy adhesives have high workability, and cured products thereof are excellent in adhesiveness, electrical properties, heat resistance, moisture resistance, and other properties. As an example of applications of epoxy adhesives to endoscopes, JP2005-152461A discloses a three-component reactive adhesive for an endoscope containing a base resin formed of an epoxy resin, such as a bisphenol A epoxy resin, with a specific amount of rubber and/or plastic added, a specific amount of amine curing agent, and a specific amount of cationic thermosetting initiator.

SUMMARY OF THE INVENTION

In a treatment using an endoscope, an insertion section of the endoscope is inserted into a body cavity, an observation target such as the inner wall of an organ or an affected area such as a tumor (hereinafter, the observation target and the affected area are collectively referred to as the "affected area or the like") is photographed to obtain information of the affected area or the like, and, if necessary, the affected area is, for example, resected with a treatment tool, such as forceps or an injection needle, put out of a forceps port disposed at the tip portion of the insertion section. To smoothly and reliably deliver an insertion of the endoscope section to the affected area or the like and obtain detailed information on the affected area or to perform a highly accurate treatment using the endoscope, it is necessary to increase the flexibility with respect to bending (bending resistance) of the insertion section to improve operability.

However, a cured product of the adhesive disclosed in JP2005-152461A has insufficient flexibility, and if the cured product is elongated when an insertion section of an endoscope to which the adhesive is applied is bent to a high curvature, cracking or breakage may occur.

Thus, an object of the present invention is to provide an adhesive for an endoscope and a cured product thereof. The adhesive has great flexibility in the state of being used for fixation of an endoscope member and is suitable for fixation of the endoscope member. Another object of the present invention is to provide an endoscope including the cured product as a member for fixing an endoscope member and having great flexibility. Still another object of the present invention is to provide a method for producing an endoscope by using the adhesive for an endoscope.

The above objects have been achieved by the following means.

<1> A two-component adhesive for an endoscope includes a base resin and a curing agent.

The base resin contains an epoxy resin (A), and the epoxy resin (A) includes an epoxy resin (a) having an average degree of polymerization of 2 or more.

<2> In the adhesive for an endoscope according to <1>, the epoxy resin (a) is at least one of (a1) to (a4) below.
  (a1) An epoxy resin having a polyester structure
  (a2) An epoxy resin having a polyurethane structure
  (a3) An epoxy resin having an acrylonitrile-derived constituent and a 1,3-butadiene-derived constituent
  (a4) An epoxy resin having a polybutadiene structure

<3> In the adhesive for an endoscope according to <1> or <2>, a content of the epoxy resin (a) in the epoxy resin (A) is 5 to 95 mass %.

<4> In the adhesive for an endoscope according to any one of <1> to <3>, the curing agent includes a polyamine compound (B).

<5> In the adhesive for an endoscope according to <4>, the polyamine compound (B) is polyamidoamine or a polyamine compound represented by general formula (I) or (II) below.

General Formula (I)

General Formula (II)

In general formula (I), n represents an integer of 1 to 3. $L^1$ represents an aliphatic or alicyclic hydrocarbon group with a valence of n+1, an aromatic hydrocarbon group with a valence of n+1, a group with a valence of n+1 formed of a combination of an aliphatic or alicyclic hydrocarbon group and an aromatic hydrocarbon group, or a group with a valence of n+1 having an aliphatic hydrocarbon chain into which at least one oxygen or nitrogen atom is incorporated.

In general formula (II), $L^2$ represents an alkylene group, —O—, —$SO_2$—, or a divalent group formed of a combination thereof, and $L^3$ and $L^4$ each independently represent an arylene group.

<6> In the adhesive for an endoscope according to any one of <1> to <5>, the adhesive is used in the form of a mixture of the base resin and the curing agent with the curing agent being present in an amount of 10 to 75 parts by mass based on 100 parts by mass of the base resin.

<7> In the adhesive for an endoscope according to any one of <1> to <6>, the adhesive is used to fix a member in a tip portion of an insertion section of the endoscope.

<8> In the adhesive for an endoscope according to any one of <1> to <6>, the adhesive is used to coat a string tightly bound around a connected portion of an insertion section of the endoscope.

<9> In the adhesive for an endoscope according to any one of <1> to <6>, the adhesive is used to seal peripheries of an observation window and an illumination window in a tip portion of an insertion section of the endoscope.

<10> In the adhesive for an endoscope according to any one of <1> to <6>, the adhesive is used to fix a prism in an optical device constituting the endoscope.

<11> A cured product is formed by curing the adhesive for an endoscope according to any one of <1> to <10>.

<12> An endoscope includes the cured product according to <11> and a member fixed with the cured product.

<13> A method for producing an endoscope includes fixing a member by using the adhesive for an endoscope according to any one of <1> to <10>.

In the description of the present invention, "to" is meant to include the numerical values before and after "to" as the lower and upper limits.

In the description of the present invention, when the number of carbon atoms of a group is specified, the number of carbon atoms means the number of carbon atoms of the whole group. That is, when the group further has a substituent, the number of carbon atoms means the number of carbon atoms of the whole including the substituent.

The adhesive for an endoscope according to the present invention has great flexibility in the state of being used for fixation of a member. The cured product according to the present invention has great flexibility. Therefore, the endoscope according to the present invention, which has the cured product as a member that fixes an endoscope member, also has great flexibility. According to the method for producing an endoscope according to the present invention, the endoscope according to the present invention can be obtained.

DESCRIPTION OF THE PREFERRED EMBODIMENTS

Adhesive for Endoscope

An adhesive for an endoscope according to the present invention is a two-component adhesive that includes a base resin and a curing agent separate from each other (that is composed of a formulation including the base resin and a formulation including the curing agent).

The base resin contains an epoxy resin (A), and the epoxy resin (A) includes an epoxy resin (a) having an average degree of polymerization of 2 or more.

The curing agent includes a curing component that acts on the epoxy resin (A) having two or more epoxy groups to cure the epoxy resin (A) (a component that acts on an epoxy resin to cure the epoxy resin).

The adhesive for an endoscope according to the present invention is used to fix at least one of a resin member (the resin member includes a rubber member), a metal member, or a glass member (a resin member, a metal member, and/or a glass member) constituting the endoscope. The "fixing" is performed by bonding at least one of the resin member, the metal member, or the glass member to, for example, a supporting member constituting the endoscope. The supporting member may be a tube wall or the like of the endoscope or an immovable member fixed to the tube wall or the like, or may be a member whose relative position in the endoscope can be moved like a tube. In the present invention, the term "fixing" is meant to include filling, that is, sealing, with a cured adhesive, a space between the above member constituting the endoscope and the supporting member incorporated with the above member.

Hereinafter, the "adhesive for an endoscope" may be referred to simply as the "adhesive". A fixing portion or a sealing portion formed of the above cured adhesive between a member and a member may be referred to as an adhesive joint.

Epoxy Resin (A)

The epoxy resin (A) includes an epoxy resin (a) having an average degree of polymerization of 2 or more. That is, the epoxy resin (a) has a polymer structure, and the average of the number of constituents of the polymer structure is 2 or more.

Examples of the polymer structure include structures formed by condensation polymerization or polyaddition (successive polymerization) of monomers, such as polyester structures, polyurethane structures, polyamide structures, polyurea structures, and polyether structures. Alternatively, the polymer structure may be formed by addition polymerization (chain polymerization) of monomers.

The content of the epoxy resin (a) in the epoxy resin (A) may be 100 mass %. To provide a cured product with further improved breaking strength, the content of the epoxy resin (a) in the epoxy resin (A) is preferably 1 mass or more, more preferably 5 mass % or more. The upper limit is preferably 99 mass % or less, more preferably 95 mass % or less.

To provide a cured product with further improved breaking strength, the epoxy resin (A) preferably includes an epoxy resin having an average degree of polymerization of more than 1 and less than 2 (preferably 1.8 or less, more preferably 1.6 or less). Examples of the epoxy resin having an average degree of polymerization of more than 1 and less than 2 include epoxy resins having an average degree of polymerization of more than 1 and less than 2 among epoxy resins (b) described later. When the epoxy resin (A) includes an epoxy resin having an average degree of polymerization of more than 1 and less than 2, for improved breaking strength, the content of the epoxy resin having an average degree of polymerization of more than 1 and less than 2 in the epoxy resin (A) is preferably 1 mass % or more, more preferably 5 mass % or more, still more preferably 10 mass % or more. The upper limit is preferably 99 mass % or less, more preferably 95 mass % or less, still more preferably 90 mass % or less.

Epoxy Resin (a)

The epoxy resin (a) may be any epoxy resin that has an average degree of polymerization of 2 or more, and the average degree of polymerization is preferably 2 to 20, more preferably 2 to 10.

The epoxy resin (a) preferably includes an epoxy resin having a degree of polymerization of 3 or more (an epoxy resin having a polymer structure composed of 3 or more constituents). The proportion of the epoxy resin (a) accounted for by the epoxy resin having a degree of polymerization of 3 or more is preferably 10 mol % or more, more preferably 20 mol % or more.

When the constituents included in the epoxy resin (a) are present in the form of repeating units, they may be in block or random form.

In the description of the present invention, the "degree of polymerization" of the epoxy resin (a) means the number of constituents. The "constituent" means a repeating unit in the case of polymers formed by successive polymerization and means a monomer-derived component in the case of polymers formed by chain polymerization. The average degree of polymerization refers to a number average degree of polymerization.

The average degree of polymerization can be calculated from a number average molecular weight of the epoxy resin (a) in terms of polystyrene determined by gel permeation chromatography (GPC). An HLC-8220 (trade name, manufactured by Tosoh Corporation) GPC apparatus is used. As an eluent, various solvents that can dissolve epoxy resin can be used. For example, tetrahydrofuran can be used. Columns of TSKgel SuperHZ series are suitable for use. A single column may be used, or a plurality of columns can be used in combination as required. For example, using TSKgel SuperHZ2500 and TSKgel SuperHZ1000 (trade names, manufactured by Tosoh Corporation) in combination, detection can be performed with a refractive index (RI) detector at 25° C. and a flow rate of 0.5 mL/min. As the epoxy resin (a), a commercially available product or an epoxy resin synthesized by a conventional method may be used.

A cured product formed by subjecting the adhesive according to the present invention to curing reaction has a high elongation at break and great flexibility. Therefore, when the cured product is used for an insertion section of an endoscope, the insertion section can be provided with sufficient bending resistance (can be resistant to cracking and breakage). Although not clear, the reasons for this are presumably as follows.

The epoxy resin (a) used for the base resin of the adhesive according to the present invention includes, in its molecular structure, a constituent having an average degree of polymerization at or above a certain level and thus has a flexible structure. That is, a plurality of epoxy groups reactive with the curing component in the curing agent are present with a flexible molecular chain disposed therebetween. Hence, the density of the cured product cannot be excessively high, and the motility of the molecular chain is moderately increased; thus, the cured product obtained is provided with a certain degree of flexibility.

To further improve sterilization resistance of the cured product, the epoxy resin (a) is preferably at least one of (a1) to (a4) below.

(a1) An epoxy resin having a polyester structure
(a2) An epoxy resin having a polyurethane structure
(a3) An epoxy resin having an acrylonitrile-derived constituent and a 1,3-butadiene-derived constituent
(a4) An epoxy resin having a polybutadiene structure Hereinafter, the above epoxy resins are also referred to as the "epoxy resin (a1)", the "epoxy resin (a2)", the "epoxy resin (a3)", and the "epoxy resin (a4)".

For the epoxy resin (a1) and the epoxy resin (a2), in the cured product, polymer chains come close to each other due to interaction, whereby in a sterilization treatment, highly reactive molecules such as hydroxy radicals generated upon decomposition of ethylene oxide gas or hydrogen peroxide are hindered from approaching reactive moieties in the cured product, thus probably improving the sterilization resistance.

For the epoxy resin (a3) and the epoxy resin (a4), skeletons constituting these resins have low reactivity, thus probably improving the sterilization resistance.

The epoxy resin (a1) can be obtained, for example, by reacting an epoxy resin (b) described later with a polyester having a functional group (e.g., an amino group, a hydroxy group, or an acid group (e.g., a carboxy group)) that can react with an epoxy group.

Examples of commercially available products of the epoxy resin (a1) include EPOKEY 701HV (trade name, manufactured by Mitsui Chemicals, Inc.).

In the epoxy resin (a1), the molecular weight of a molecular chain between ester bonds is preferably 50 to 1000, more preferably 50 to 800, still more preferably 50 to 500.

The epoxy resin (a2) can be obtained, for example, by reacting a polyisocyanate compound or a monoisocyanate compound with a compound obtained by reacting an epoxy resin (b) described later with a polyhydroxy compound.

Examples of commercially available products of the epoxy resin (a2) include ADEKA RESIN EPU-73B (trade name, manufactured by ADEKA CORPORATION).

In the epoxy resin (a2), the molecular weight of a molecular chain between urethane bonds is preferably 50 to 1000, more preferably 50 to 800, still more preferably 50 to 500.

The epoxy resin (a3) has two or more epoxy groups in its molecule and has, as a skeleton, a molecular chain constituted by an acrylonitrile-derived constituent and a 1,3-butadiene-derived constituent. The skeleton is preferably derived, for example, from a copolymer obtained by copolymerizing a carboxy-containing monomer such as acrylic acid or methacrylic acid with an acrylonitrile-butadiene rubber resulting from reaction of acrylonitrile and 1,3-butadiene. The mass average molecular weight of the copolymer and the polymerization ratio of the starting monomer are not particularly limited. By reacting the copolymer with, for example, an epoxy resin (b) described later, the epoxy resin (a3) can be obtained. Preferably, the epoxy resin (a3) does not include an ester bond or a urethane bond in the molecular chain including the above skeleton, that is, the main chain (typically, the longest chain) of the epoxy resin (a3). The epoxy resin (a3) may have an ester bond or a urethane bond in its side chain.

Examples of commercially available products of the epoxy resin (a3) include ADEKA RESIN EPR-1415-1 (trade name, manufactured by ADEKA CORPORATION).

The epoxy resin (a4) may be any resin having two or more epoxy groups in its molecule and whose skeleton is a molecular chain derived from a butadiene rubber. The mass average molecular weight of the butadiene rubber is not particularly limited. Preferably, the epoxy resin (a4) does not include an ester bond or a urethane bond in the molecular chain including the above skeleton, that is, the main chain (typically, the longest chain) of the epoxy resin (a4). The epoxy resin (a4) may have an ester bond or a urethane bond in its side chain. Preferably, the epoxy resin (a4) does not have an acrylonitrile-derived constituent.

Examples of commercially available products of the epoxy resin (a4) include DENALEX R-15EPT (trade name, manufactured by Nagase ChemteX Corporation).

Epoxy Resin (b)

The epoxy resin (A) used in the present invention may include an epoxy resin (b). The epoxy resin (b) is not particularly limited and may be any epoxy resin commonly used as a base resin of an epoxy adhesive. Examples of the epoxy resin (b) include bisphenol A epoxy resins, bisphenol F epoxy resins, and phenol novolac epoxy resins.

The bisphenol A epoxy resin used in the present invention is not particularly limited and may be any bisphenol A epoxy resin commonly used as a base resin of an epoxy adhesive. Specific examples include bisphenol A diglycidyl ethers (e.g., "jER825", "jER828", and "jER834" (trade names) manufactured by Mitsubishi Chemical Corporation) and bisphenol A propoxylate diglycidyl ethers.

The bisphenol F epoxy resin used in the present invention is not particularly limited and may be any bisphenol F epoxy resin commonly used as a base resin of an epoxy adhesive. Specific examples include bisphenol F diglycidyl ethers (e.g., "EPICLON 830" (trade name) manufactured by DIC Corporation) and 4,4'-methylenebis(N,N-diglycidylaniline).

The phenol novolac epoxy resin used in the adhesive according to the present invention is not particularly limited and may be any phenol novolac epoxy resin commonly used as a base resin of an epoxy adhesive. Specific examples include product number 406775 manufactured by Sigma-Aldrich.

These epoxy resins may be used alone or in combination.

The content of the epoxy resin (A) in the base resin is preferably 80 mass % or more, more preferably 90 mass % or more, and may be 100 mass %. The base resin may include at least one of a solvent, a plasticizer, an adhesion improver (e.g., a silane coupling agent), a surfactant, a colorant (e.g., a pigment or a dye), a weathering agent, an antioxidant, a heat stabilizer, a lubricant, an antistatic agent, a whitener, a release agent, a conductive agent, a viscosity regulator, a filler (e.g., silica or calcium carbonate), a thixotropy-imparting agent, a diluent, or a flame retardant as long as the effects of the present invention are not impaired.

Curing Component

In the adhesive according to the present invention, various curing agents known as curing components of epoxy adhesives can be used. For example, acid anhydride compounds, imidazole compounds, phosphorus compounds, thiol compounds, dicyandiamide compounds, phenolic compounds, and polyamine compounds can be used. Of these, a single curing agent may be used alone, or two or more curing agents may be used in combination.

In the present invention, the curing agent preferably includes a polyamine compound. By curing the adhesive with a polyamine compound, a crosslinked structure is formed that is more stable to disinfectants such as peracetic acid used for endoscopes. Hereinafter, a polyamine compound included in the curing agent of the present invention is also referred to as a "polyamine compound (B)".

Polyamine Compound (B)

The polyamine compound (B) is preferably a polyamidoamine or a polyamine compound represented by general formula (I) or (II) below.

General Formula (I)

General Formula (II)

In general formula (I), n represents an integer of 1 to 3. $L^1$ represents an aliphatic or alicyclic hydrocarbon group with a valence of n+1, an aromatic hydrocarbon group with a valence of n+1, a group with a valence of n+1 formed of a combination of an aliphatic or alicyclic hydrocarbon group and an aromatic hydrocarbon group, or a group with a valence of n+1 having an aliphatic hydrocarbon chain into which at least one oxygen or nitrogen atom is incorporated.

In general formula (II), $L^2$ represents an alkylene group, —O—, —$SO_2$—, or a divalent group formed of a combination thereof, and $L^3$ and $L^4$ each independently represent an arylene group.

The "group with a valence of n+1 formed of a combination of an aliphatic or alicyclic hydrocarbon group and an aromatic hydrocarbon group" is preferably a group formed of a combination of an "aliphatic or alicyclic hydrocarbon group with a valence of n+1" and an "aromatic hydrocarbon group with a valence of n+1".

When n is 1, the divalent aliphatic or alicyclic hydrocarbon group represented by $L^1$ is preferably an alkylene group. The divalent group represented by $L^1$ and having an aliphatic hydrocarbon chain into which at least one oxygen or nitrogen atom is incorporated is preferably a group formed of a combination of an alkylene group and a polyoxyalkylene group or a group formed of a combination of an alkylene group and an imino group.

When n is 2, the trivalent aliphatic or alicyclic hydrocarbon group represented by $L^1$ is preferably an alkanetriyl group, and the trivalent group represented by $L^1$ and having an aliphatic hydrocarbon chain into which at least one oxygen atom is incorporated is preferably a trivalent group formed of a combination of an alkanetriyl group and three polyoxyalkylene groups.

When n is 3, the tetravalent aliphatic or alicyclic hydrocarbon group represented by $L^1$ is preferably an alkanetetrayl group, and the tetravalent group represented by $L^1$ and having an aliphatic hydrocarbon chain into which at least one oxygen atom is incorporated is preferably a tetravalent group formed of a combination of an alkanetetrayl group and four polyoxyalkylene groups.

n is preferably 1 or 2.

In general formula (I), the alkylene group may be linear or cyclic. Cyclic alkylene groups include alkylene groups including a saturated alicycle. The number of carbon atoms of the alkylene group is preferably 1 to 20, more preferably 5 to 12. Specific examples of the alkylene group include methylene, ethylene, hexamethylene, 2,4,4-trimethylhexamethylene, 2-methylpentamethylene, cyclohexylene, dodecamethylene, methylene-cyclohexylene, and methylene-cyclohexylene-methylene. Specific examples of the "alkylene groups including a saturated alicycle" include methylene-cyclohexylene and methylene-cyclohexylene-methylene.

The alkylene group of an oxyalkylene group of a polyoxyalkylene group is as defined for the above alkylene group, and preferred ranges thereof are also the same as those of the above alkylene group. The number of repetitions of the oxyalkylene group is preferably an integer of 1 to 20.

The number of carbon atoms of the aromatic hydrocarbon group is preferably 6 to 14, more preferably 6 to 10. Specific examples of divalent aromatic hydrocarbon groups (arylene groups) include phenylene and naphthylene. Specific examples of trivalent aromatic hydrocarbon groups (arenetriyl groups) include benzenetriyl and naphthalenetriyl. Specific examples of tetravalent aromatic hydrocarbon groups (arenetetrayl groups) include benzenetetrayl and naphthalenetetrayl.

The alkanetriyl group may be linear or cyclic. Cyclic alkanetriyl groups include alkanetriyl groups including a saturated alicycle. The number of carbon atoms of the alkanetriyl group is preferably 1 to 20, more preferably 1 to 15, particularly preferably 1 to 10. Examples include methanetriyl, ethanetriyl, propanetriyl, butanetriyl, t-butanetriyl, and cyclohexanetriyl. Specific examples of the "alkanetriyl groups including a saturated alicycle" include alkanetriyl groups formed of a combination of a cyclohexanetriyl group and three methylene groups.

The alkanetetrayl group may be linear or cyclic. Cyclic alkanetetrayl groups include alkanetetrayl groups including a saturated alicycle. The number of carbon atoms of the alkanetetrayl group is preferably 1 to 20, more preferably 1 to 15, particularly preferably 1 to 10. Examples include methanetetrayl, ethanetetrayl, propanetetrayl, t-butanetetrayl, and cyclohexanetetrayl. Specific examples of the "alkanetetrayl groups including a saturated alicycle" include alkanetetrayl groups formed of a combination of a cyclohexanetetrayl group and four methylene groups.

In general formula (II), the alkylene group may be linear or cyclic. Cyclic alkylene groups include alkylene groups including a saturated alicycle. The number of carbon atoms of the alkylene group is preferably 1 to 20, more preferably 1 to 12. Specific examples of the alkylene group include ethylene, hexamethylene, 2,4,4-trimethylhexamethylene, 2-methylpentamethylene, cyclohexylene, dodecamethylene, and methylene-cyclohexylene-methylene.

The arylene groups represented by $L^3$ and $L^4$ are as defined for the above divalent aromatic hydrocarbon groups (arylene groups), and preferred ranges thereof are also the same as those of the above divalent aromatic hydrocarbon groups.

$L^1$ to $L^4$ may each have a substituent, and specific examples of the substituent include alkyl groups. The number of carbon atoms of the alkyl groups is preferably 1 to 12, more preferably 1 to 8, particularly preferably 1 to 5. Specific examples of the alkyl groups include methyl, ethyl, n-butyl, i-propyl, s-butyl, t-butyl, t-pentyl, t-hexyl, and t-octyl. Of these, methyl is preferred.

The molecular weight of $L^1$ is preferably 60 to 1000, more preferably 80 to 500.

The molecular weight of $L^3$—$L^2$—$L^4$ is preferably 180 to 1000, more preferably 180 to 500.

When $L^1$ to $L^4$ have a substituent, the molecular weight of the substituent is also included in the above molecular weight.

In the present invention, the polyamine compound (B) represented by general formula (I) is more preferred. The polyamine compound (B) represented by general formula (I) is unlikely to react with hydroxyl radicals generated upon ethylene oxide gas sterilization treatment or hydrogen peroxide plasma sterilization treatment and further improves sterilization resistance, and thus the following embodiments are more preferred.

When n=1, $L^1$ preferably represents an alkylene group, a group formed of a combination of an alkylene group and an imino group, or a group formed of a combination of an alkylene group and a polyoxyalkylene group, more preferably represents a group formed of a combination of an alkylene group and a polyoxyalkylene group.

When n=2, $L^1$ preferably represents an alkanetriyl group or a trivalent group formed of a combination of an alkanetriyl group and three polyoxyalkylene groups, more preferably represents a trivalent group formed of a combination of an alkanetriyl group and three polyoxyalkylene groups.

When n=3, $L^1$ preferably represents an alkanetetrayl group or a tetravalent group formed of a combination of an alkanetetrayl group and four polyoxyalkylene groups, more preferably represents a tetravalent group formed of a combination of an alkanetetrayl group and four polyoxyalkylene groups.

In the above preferred embodiments, when the alkylene group, the alkanetriyl group, and the alkanetetrayl group in $L^1$ are linear, the polyamine-derived constituent in the cured product has high motility, and the elongation at break can be further improved.

Specific examples of the polyamine compound (B) used in the present invention will be described below, but the present invention is not limited thereto.

(B-1)

(B-2)

(B-3)

(B-4)

(B-5)

(B-6)

t = 6.1 x + y + z = 5~6

(B-7)

(B-8)

In the present invention, a single polyamine compound (B) may be used alone, or two or more polyamine compounds (B) may be used in combination.

In the present invention, the proportion of the curing component in the curing agent accounted for by the polyamine compound (B) is preferably 80 mass % or more, more preferably 90 mass % or more. The polyamine compound (B) may account for all of the curing component in the curing agent.

The curing agent may be composed of the above-described curing component or may include, in addition to the above-described curing component, a solvent, a filler, a plasticizer, a viscosity modifier, and the like as long as the effects of the present invention are not impaired. The content of the curing component in the curing agent is preferably 80 mass % or more, more preferably 90 mass % or more.

The adhesive according to the present invention is preferably used in the form of a mixture of 100 parts by mass of the epoxy resin (A) constituting the base resin and 10 to 75 parts by mass, more preferably 10 to 50 parts by mass, of the curing component (preferably, the polyamine compound (B)) constituting the curing agent.

In the adhesive according to the present invention, the epoxy resin (A) constituting the base resin and the polyamine compound (B) constituting the curing agent are preferably used in the form of a mixture in an amount of 0.1 to 1.5 equivalents, more preferably 0.3 to 1.0 equivalent, particularly preferably 0.5 to 1.0 equivalent, in terms of active hydrogen equivalents relative to the epoxy equivalent.

When the amount of curing agent used is in the above range, the cured product obtained by curing the adhesive can be provided with high sterilization resistance.

Cured Product

A cured product according to the present invention is formed by curing the adhesive according to the present invention. That is, the cured product according to the present invention is used as a member constituting an adhesive joint of an endoscope. The cured product according to the present invention can be obtained by mixing the base resin and the curing agent of the adhesive according to the present invention and then curing the mixture, for example, by heating at −20° C. to 150° C. for 10 minutes to 72 hours. The mixing of the base resin and the curing agent may be performed in the usual manner. The mixing is preferably performed while removing bubbles, and thus is usually performed under reduced pressure. If the curing temperature is high, the endoscope will be exposed to high temperature for many times during the manufacturing process, and thus the curing temperature is preferably as low as possible. From this viewpoint, the curing temperature is preferably 100° C. or lower, more preferably 80° C. or lower. For the curing reaction to sufficiently proceed, the curing temperature is preferably 0° C. or higher, more preferably 10° C. or higher.

Endoscope

An endoscope according to the present invention has an adhesive joint between a fixed member and a resin member, a metal member, or a glass member, the adhesive joint being formed of the cured product according to the present invention.

An example of the endoscope (electronic endoscope) according to the present invention will be described. Electronic endoscopes are incorporated with a flexible tube for an endoscope (hereinafter a flexible tube for an endoscope may be referred to simply as a "flexible tube") and are widely used as medical instruments. In the example illustrated in FIG. 1, an electronic endoscope 2 includes an insertion section 3 to be inserted into a body cavity, a main-body operation section 5 connected to the proximal end portion of the insertion section 3, and a universal cord 6 to be connected to a processor device or a light source device. The insertion section 3 is composed of a flexible tube 3a connected to the main-body operation section 5, an angle portion 3b connected to the flexible tube 3a, and a tip portion 3c connected to the distal end of the angle portion 3b and mainly formed of a metal (e.g., stainless steel) member. An imaging device (not illustrated) for imaging a body cavity is built in the tip portion 3c. The flexible tube 3a, which occupies most of the length of the insertion section 3, is flexible over substantially the entire length thereof. In particular, a portion to be inserted into a body cavity or the like has a more flexible structure.

Figure 1:
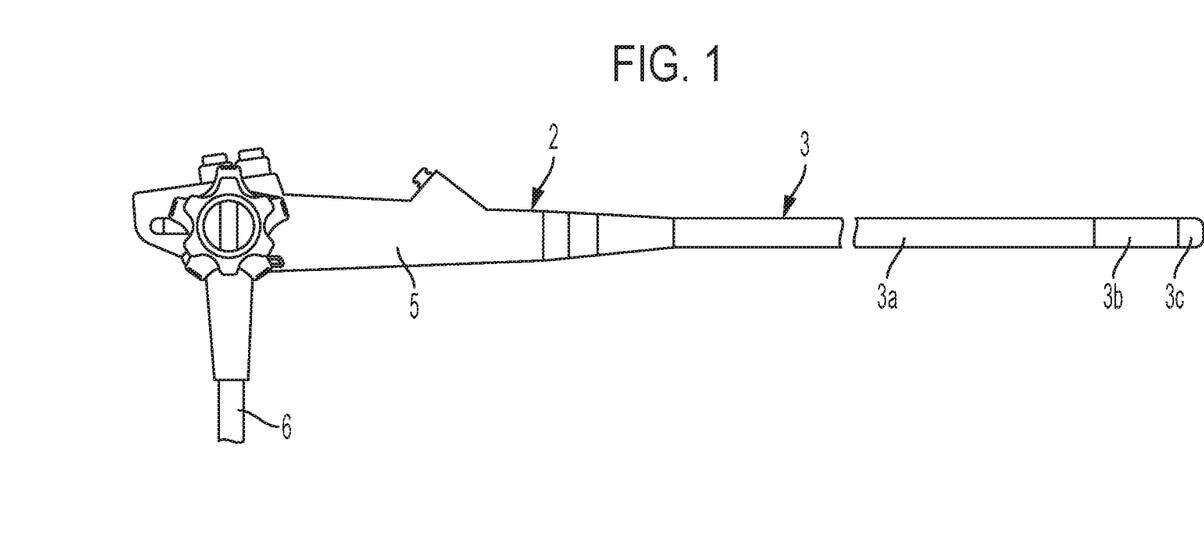
FIG. 1 is an external view illustrating a configuration of an endoscope according to an embodiment of the present invention.

In FIG. 1, a plurality of channels (not illustrated) are formed that extend from the main-body operation section 5 to the distal end surface of the tip portion 3c through the insertion section 3 along the axis direction of the insertion section 3.

Figure 2:
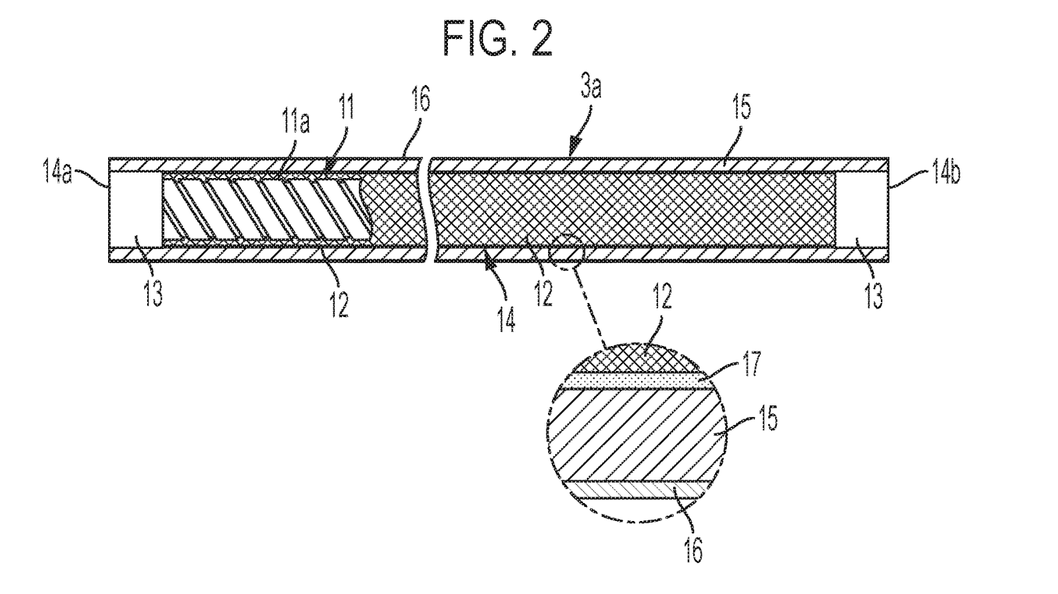
FIG. 2 is a partial sectional view illustrating a configuration of an insertion section of the endoscope illustrated in FIG. 1.

The flexible tube 3a in FIG. 1 is configured such that a resin layer 15 covers the outer peripheral surface of a flexible tube substrate 14, as illustrated in FIG. 2.

14a is the distal side (the tip portion 3c side), and 14b is the proximal side (the main-body operation section 5 side).

The flexible tube substrate 14 includes a spiral tube 11, which is disposed on the innermost side and formed by spirally winding a metal strip 11a, and a tubular net 12, which covers the spiral tube 11 and is formed by braiding metal wires. Caps 13 are fitted to opposite ends of the flexible tube substrate 14. The resin layer 15 is bonded to the flexible tube substrate 14 with a cured adhesive layer 17 interposed therebetween. While the cured adhesive layer (adhesive joint) 17 is illustrated as a layer having a uniform thickness for convenience of illustration, the cured adhesive layer 17 need not necessarily be in such a form and may be indeterminately interposed between the resin layer 15 and the flexible tube substrate 14. The cured adhesive layer 17 may rather have substantially no thickness such that the resin layer 15 and the flexible tube substrate 14 are substantially directly bonded together.

The outer surface of the resin layer 15 is coated with a coat layer 16 having chemical resistance and containing, for example, fluorine. To clearly illustrate the layer structure, the cured adhesive layer 17, the resin layer 15, and the coat layer 16 are illustrated as being thick relative to the diameter of the flexible tube substrate 14.

Figure 3:
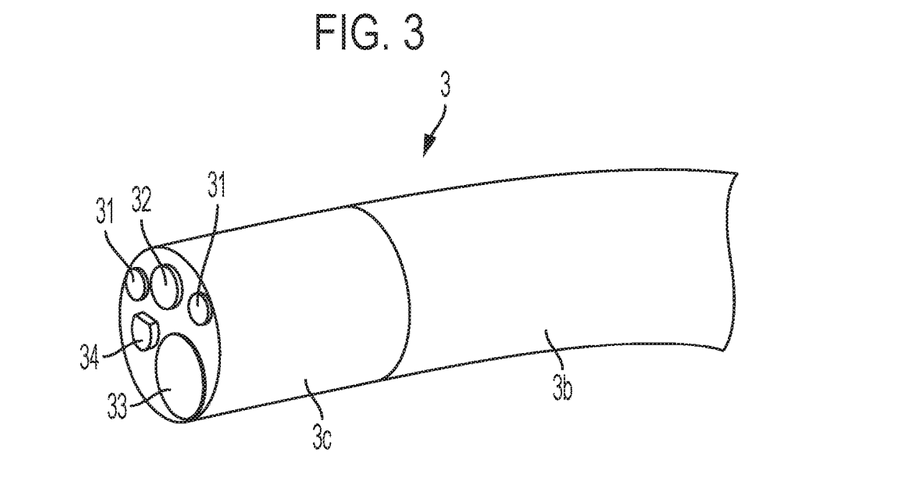
FIG. 3 is an external perspective view of a tip portion of the insertion section.

As illustrated in FIG. 3, an illumination window 31, an observation window 32, and a forceps port 33 are formed in the distal end surface of the tip portion 3c. To wash the distal end surface as required, a nozzle 34 for sending water and air is formed. The illumination window 31, the observation window 32, the forceps port 33, and the nozzle 34 communicate with the main-body operation section 5 through the channels.

Figure 4:
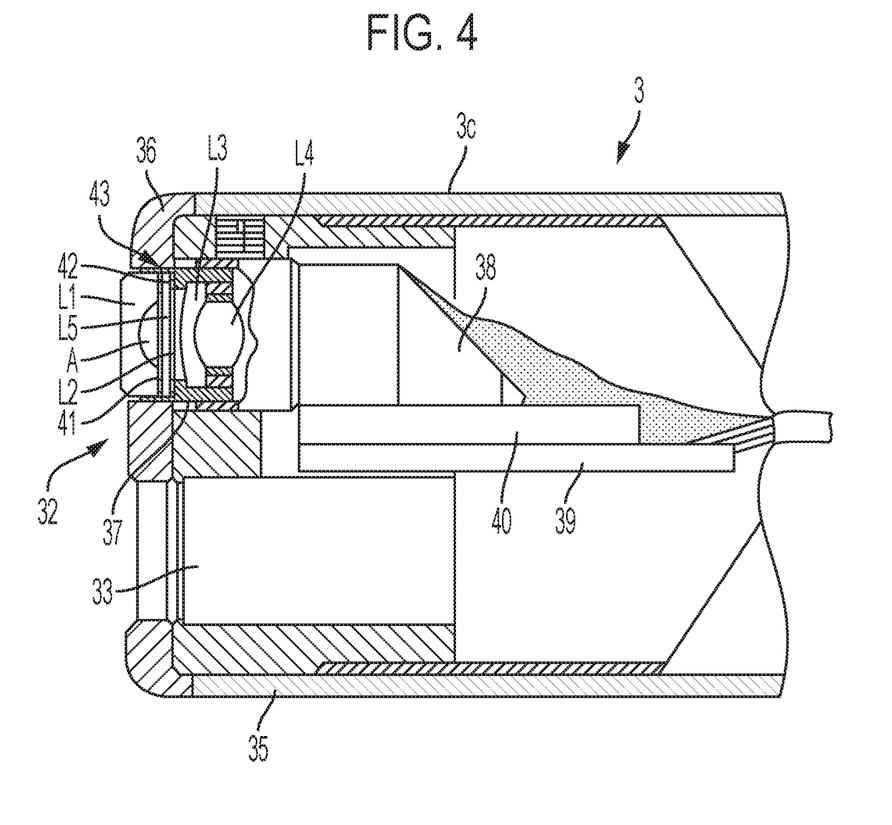
FIG. 4 is a partially cut-away partial sectional view of the tip portion, without hatching that shows sections of lenses and a prism.

As illustrated in FIG. 4, the tip portion 3c is composed of a tip-portion main body 35 made of metal and an end cap 36 made of an electrically insulating material.

An observation unit 43, which is an optical device, is disposed in the observation window 32. The observation unit 43 includes a lens holder 37, and in the lens holder 37, an objective optical system composed of lenses L1 to L5 is fixed with cured adhesives 41 and 42. In the objective optical system, A is an air layer. A prism 38 is bonded and fixed to an end face of the lens holder 37. The optical axis of the objective optical system can be bent at a right angle by the prism 38. The prism 38 is bonded to a solid-state imaging element 40. The solid-state imaging element 40 is fixed to a substrate 39.

Method for Producing Endoscope

A method for producing an endoscope according to the present invention is not particularly limited as long as the method includes fixing at least one of a resin member, a metal member, or a glass member by using the adhesive according to the present invention. For steps other than fixing of at least one of a resin member, a metal member, or a glass member, usual production steps may be employed to produce the endoscope according to the present invention. For example, the method for producing an endoscope according to the present invention preferably includes a step of mixing the base resin and the curing agent of the adhesive according to the present invention under reduced pressure, then injecting or applying the adhesive according to the present invention into or to a target portion, and heating the adhesive at −20° C. to 150° C. (preferably 0° C. to 100° C., more preferably 10° C. to 80° C.) for 10 minutes to 72 hours (preferably 30 minutes to 48 hours, more preferably 1 to 24 hours).

Use of Adhesive

The adhesive according to the present invention is used to fix at least one of a resin member, a metal member, or a glass member constituting an insertion section of an endoscope to another member constituting the endoscope. That is, the fixing is performed by bonding at least one of the resin member, the metal member, or the glass member to a supporting member (e.g., a resin member, a glass member, or a metal member). Preferably, the adhesive according to the present invention is used, for example, to fix a resin member to a metal member, to fix a metal member to a resin member, to fix a metal member to another metal member, to fix a glass member to a metal member, or to fix a glass member to a resin member.

Specific examples of how the adhesive according to the present invention is used will be described below, but the present invention is not limited to these examples.

Examples of resin members include tubes inserted into an insertion section of an endoscope. The tubes include various tubes produced using various materials such as fluorocarbon resins such as Teflon (registered trademark), resins such as polysulfone resins, polyester resins, polyolefin resins, and silicone resins, and rubber. The adhesive according to the present invention can be used, for example, to bond a metal member or a glass member constituting an insertion section of an endoscope to any of the above tubes (to fix the metal member or the glass member to any of the above tubes).

The adhesive according to the present invention can also be used to form the cured adhesive layer 17 in FIG. 2. The adhesive according to the present invention can also be used to bond together the resin layer 15 and the coat layer 16 in FIG. 2.

The adhesive according to the present invention can be used for outer-surface finishing and fixing of an end of a flexible outer cover tube (the resin layer 15) (the end on the distal side (the angle portion 3b side) of the flexible tube 3a). Specifically, the flexible tube 3a and the angle portion 3b are bonded together using the adhesive according to the present invention. A string is tightly wound around a portion of the flexible tube 3a near the adhesive joint, a portion of the angle portion 3b near the adhesive joint, and the adhesive joint to reinforce the bonding. The configuration in which the outermost layer on the distal-side end of the flexible tube 3a and the flexible tube 3a side end of the angle portion 3b is formed of the adhesive according to the present invention reduces the likelihood of raveling of the string and facilitates the insertion of the insertion section into a body cavity. The insertion section thus formed can maintain a bright appearance after sterilization. The adhesive according to the present invention can be used for at least one of bonding of the tip portion 3c and the angle portion 3b or bonding of the insertion section 3 and the main-body operation section 5. Specifically, the tip portion 3c and the angle portion 3b are bonded together using the adhesive according to the present invention. A string is tightly wound around a portion of the tip portion 3c near the adhesive joint, a portion of the angle portion 3b near the adhesive joint, and the adhesive joint to reinforce the bonding. In the same manner as described above, the adhesive is applied so as to coat the string and cured. The bonding of the insertion section 3 and the main-body operation section 5 is performed in the same manner.

That is, the adhesive according to the present invention can be used to coat a string tightly bound around a connected portion of an insertion section of an endoscope.

The adhesive according to the present invention can also be used with reference to, for example, the description in paragraph [0037] of JP2011-212337A.

Preferably, the adhesive according to the present invention is used to fix various tubes inserted into an insertion section of an endoscope to at least one of the tip portion 3c or the main-body operation section 5.

The adhesive according to the present invention is preferably used for the tip portion 3c. Among the uses for the tip portion 3c, the adhesive according to the present invention is preferably used to seal the illumination window 31 and the observation window 32 (to fix the glass members to the end cap 36 (resin member)). This is because a thick coating of the adhesive according to the present invention can smoothly fix the outer corners of the lenses without steps and block the entrance of light from the lateral sides of the lenses.

The adhesive according to the present invention can be used to fix at least one of a metal member or a glass member, for example, to assemble the imaging device built in the tip portion 3c, to bond parts together, or to seal the solid-state imaging element 40. The imaging device has an optical system composed of a plurality of optical parts, such as the lenses L1 to L5 and the prism 38, and has the solid-state imaging element 40, such as a charge coupled device (CCD), that photoelectrically converts an optical image formed by the optical system into an imaging signal. The adhesive according to the present invention can be used, for example, for at least one of bonding of optical parts including the lenses L1 to L5 and the prism 38 made of materials such as glass or bonding of the lenses L1 to L5 and the prism 38 to the substrate 39 made of resin or metal. This bonding can fix the glass members and can fix the metal member.

The adhesive according to the present invention can be used for bond-fixing and sealing of the solid-state imaging element 40 and the substrate 39. This bonding can fix the metal members constituting the solid-state imaging element, the substrate, and the like.

EXAMPLES

The present invention will now be described in more detail with reference to examples. These examples should not be construed as limiting the present invention. "Room temperature" means 25° C.

Example 1

Production of Sheet-Like Cured Product

Using a "THINKY MIXER ARV-310 (trade name, manufactured by THINKY CORPORATION)", 100 parts by mass of an epoxy resin (A-1) (an epoxy resin having a polyester structure (EPOKEY 701HV (trade name), the average degree of polymerization of the polyester structure: 2 to 10, manufactured by Mitsui Chemicals, Inc.)) serving as a base resin and 20.1 parts by mass of a polyamine compound (13-7) (Polyoxyalkylenediamine T403 (trade name, manufactured by Mitsui Fine Chemicals, Inc., active hydrogen equivalent: 73)) serving as a curing agent were defoamed for 3 minutes with stirring at 2000 rpm under a reduced pressure of 1.0 Pa at room temperature to obtain a mixture. The mixture was cured at 80° C. for 6 hours with a MINI TEST PRESS (manufactured by Toyo Seiki Seisaku-sho, Ltd.) to obtain a sheet-like cured product 100 mm long×100 mm wide×0.4 mm thick.

Examples 2 to 20

Comparative Examples 1 to 4

Production of Sheet-Like Cured Products

Sheet-like cured products of Examples 2 to 20 and Comparative Examples 1 to 4 were produced in the same manner as the sheet-like cured product of Example 1 except that the composition, the curing temperature, and the curing time were changed as shown in Tables 1 and 2 given below.

Elongation at Break Test

The above sheet-like cured products were each subjected to a tensile test using an Autograph AGS-X (trade name, manufactured by Shimadzu Corporation) with one side held from end to end and the opposite side held from end to end, and evaluated for the elongation rate at break relative to the initial length ({(the length at break in the elongation direction (mm)−100 mm)/100 mm}×100, the "elongation at break" mentioned above). In the following evaluation criteria, A, B, and C are acceptable in this test. The results are shown in Table 1 given below.

Higher elongation at break indicates greater flexibility with respect to bending.

Evaluation Criteria

A: The elongation at break is 50% or more.
B: The elongation at break is 30% or more and less than 50%.
C: The elongation at break is 20% or more and less than 30%.
D: The elongation at break is less than 20%.

Sterilization Resistance Test

Using a STERRAD (registered trademark) NX (trade name, manufactured by Johnson & Johnson) advanced course, a hydrogen peroxide plasma sterilization treatment was performed on the above sheet-like cured products at room temperature. Using an Autograph AGS-X (trade name, manufactured by Shimadzu Corporation), a tensile test was performed on the sheet-like cured product before the sterilization treatment and the sheet-like cured product subjected to the sterilization treatment 100 times. The sterilization resistance was evaluated on the basis of a breaking strength retention after the sterilization treatment (100× [breaking strength (MPa) after 100 sterilization treatments]/ [breaking strength (MPa) before sterilization treatment]). In the following evaluation criteria, A, B, and C are acceptable in this test. The results are shown in Table 1 given below.

Evaluation Criteria

A: The breaking strength is 95% or more of that before a sterilization treatment.
B: The breaking strength is 90% or more and less than 95% of that before a sterilization treatment.
C: The breaking strength is 85% or more and less than 90% of that before a sterilization treatment.
D: The breaking strength is less than 85% of that before a sterilization treatment.
E: The sample is degraded and broken during a hydrogen peroxide plasma sterilization treatment, and a tensile test cannot be performed.

[Higher Breaking Strength Retentions Indicate that the Cured Product has Undergone Less Oxidation Degradation.]

TABLE 1

|  |  | Ex. 1 | Ex. 2 | Ex. 3 | Ex. 4 | Ex. 5 | Ex. 6 | Ex. 7 | Ex. 8 | Ex. 9 | Ex. 10 | Ex. 11 | Ex. 12 |
|---|---|---|---|---|---|---|---|---|---|---|---|---|---|
| Epoxy resin (a) | Type | (A-1) | (A-2) | (A-3) | (A-2) | (A-2) | (A-2) | (A-3) | (A-2) | (A-2) | (A-2) | (A-2) | (A-2) |
|  | Content | 100 | 100 | 100 | 190 | 50 | 10 | 50 | 100 | 100 | 100 | 100 | 100 |
| Epoxy resin (b) | Type |  |  |  | (A-4) | (A-4) | (A-4) | (A-4) |  |  |  |  |  |
|  | Content |  |  |  | 10.0 | 50.0 | 90.0 | 50.0 |  |  |  |  |  |
| Polyamine compound (B) | Type | (B-7) | (B-7) | (B-7) | (B-7) | (B-7) | (B-7) | (B-7) | (B-1) | (B-2) | (B-3) | (B-4) | (B-5) |
|  | Content | 20.1 | 22.5 | 35.2 | 45.3 | 33.1 | 26.4 | 37.2 | 26.9 | 21.3 | 15.3 | 19.1 | 53.8 |
| Other compound (E) | Type |  |  |  |  |  |  |  |  |  |  |  |  |
|  | Content |  |  |  |  |  |  |  |  |  |  |  |  |
| Equivalence ratio of active hydrogen to epoxy equivalent |  | 1.0 | 1.0 | 1.0 | 1.0 | 1.0 | 1.0 | 1.0 | 1.0 | 1.0 | 1.0 | 1.0 | 1.0 |
| Curing temperature | °C. | 80 | 80 | 80 | 80 | 80 | 80 | 80 | 80 | 80 | 80 | 80 | 80 |
| Curing time | hr | 6 | 6 | 6 | 6 | 6 | 6 | 6 | 6 | 6 | 6 | 6 | 6 |
| Elongation at break |  | A | A | A | A | A | A | A | B | A | A | C | C |
| Sterilization resistance |  | A | A | A | A | A | A | A | B | B | B | B | B |

|  |  | Ex. 13 | Ex. 14 | Ex. 15 | Ex. 16 | Ex. 17 | Ex. 18 | Ex. 19 | Ex. 20 | C.E. 1 | C.E. 2 | C.E. 3 |
|---|---|---|---|---|---|---|---|---|---|---|---|---|
| Epoxy resin (a) | Type | (A-2) | (A-2) | (A-2) | (A-2) | (A-2) | (A-2) | (A-2) | (A-5) |  |  |  |
|  | Content | 100 | 100 | 100 | 100 | 50 | 100 | 100 | 50 |  |  |  |
| Epoxy resin (b) | Type |  |  |  |  | (A-4) |  |  | (A-4) | (A-4) | (A-4) | (A-4) (A-6) |
|  | Content |  |  |  |  | 50.0 |  |  | 50.0 | 100.0 | 100.0 | 25 75 |
| Polyamine compound (B) | Type | (B-6) | (B-8) | (B-9) | (B-10) | (B-7) |  |  | (B-7) | (B-3) | (B-4) | (B-11) |
|  | Content | 26.9 | 21.3 | 15.3 | 19.1 | 16.6 |  |  | 13.4 | 13.0 | 28.0 | 60 |
| Other compound (E) | Type |  |  |  |  |  | (E-3) | (E-4) |  |  |  | (E-1) (E-2) |
|  | Content |  |  |  |  |  | 10.0 | 75.0 |  |  |  | 0.3 2 |
| Equivalence ratio of active hydrogen to epoxy equivalent |  | 1.0 | 1.0 | 1.0 | 1.0 | 1.0 | 1.0 | 1.0 | 1.0 | 1.0 | 1.0 | 1.0 |
| Curing temperature | °C. | 80 | 80 | 80 | 80 | 80 | 120 | 150 | 80 | 80 | 80 | 80 |
| Curing time | hr | 6 | 6 | 6 | 6 | 6 | 6 | 6 | 6 | 6 | 6 | 6 |
| Elongation at break |  | A | B | C | C | A | C | C | A | D | D | D |
| Sterilization resistance |  | A | B | B | B | A | C | C | A | D | E | E |

Notes of Table

Units of the contents are parts by mass.

Ex. 1 to 20 and C.E. 1 to 3: Examples 1 to 20 and Comparative Examples 1 to 3

Breaking Strength Test

The sheet-like cured products of Examples 2, 4 to 7, 17, and 20 and Comparative Example 4 were each subjected to a tensile test using an Autograph AGS-X (trade name, manufactured by Shimadzu Corporation) and evaluated for strength at break (hereinafter referred to as breaking strength). In the following evaluation criteria, A, B, and C are acceptable in this test. The results are shown in Table 2 given below.

Evaluation Criteria

A: The breaking strength is 40 MPa or more.
B: The breaking strength is 30 MPa or more and less than 40 MPa.
C: The breaking strength is 20 MPa or more and less than 30 MPa.
D: The breaking strength is less than 20 MPa.

TABLE 2

|  |  | Ex. 2 | Ex. 4 | Ex. 5 | Ex. 6 | Ex. 7 | Ex. 17 | Ex. 20 | C.E. 4 |
|---|---|---|---|---|---|---|---|---|---|
| Epoxy resin (a) | Type | (A-2) | (A-2) | (A-2) | (A-2) | (A-3) | (A-2) | (A-5) |  |
|  | Content | 100 | 90 | 50 | 10 | 50 | 50 | 50 |  |
| Epoxy resin (b) | Type |  | (A-4) | (A-4) | (A-4) | (A-4) | (A-4) | (A-4) | (A-4) |
|  | Content |  | 10.0 | 50.0 | 90.0 | 50.0 | 50.0 | 50.0 | 100.0 |
| Polyamine compound (B) | Type | (B-7) | (B-7) | (B-7) | (B-7) | (B-7) | (B-7) | (B-7) | (B-7) |
|  | Content | 22.5 | 45.3 | 33.1 | 26.4 | 37.2 | 16.6 | 13.4 | 39.4 |
| Equivalence ratio of active hydrogen to epoxy equivalent |  | 1.0 | 1.0 | 1.0 | 1.0 | 1.0 | 1.0 | 1.0 | 1.0 |
| Curing temperature | °C. | 80 | 80 | 80 | 80 | 80 | 80 | 80 | 80 |
| Curing time | hr | 6 | 6 | 6 | 6 | 6 | 6 | 6 | 6 |
| Elongation at break |  | A | A | A | A | A | A | A | D |
| Breaking strength |  | B | A | A | A | A | A | A | A |

Notes of Table
C.E. 4: Comparative Example 4

Notes of Table
Epoxy resin (A)
Epoxy resin (a)
- (A-1) An epoxy resin having a polyester structure (EPOKEY 701HV (trade name), the average degree of polymerization of the polyester structure: 2 to 10, manufactured by Mitsui Chemicals, Inc.)
- (A-2) An epoxy resin having a polyurethane structure (ADEKA RESIN EPU-73B (trade name), the average degree of polymerization of the polyurethane structure: 2 to 10, manufactured by ADEKA CORPORATION)
- (A-3) An epoxy resin having an acrylonitrile/1,3-butadiene copolymer structure (hereinafter referred to as NBR structure) (ADEKA RESIN EPR-1415-1 (trade name), the average degree of polymerization of the NBR structure: 2 to 10 (the average degree of polymerization defined in the present invention: 4 to 20), manufactured by ADEKA CORPORATION)
- (A-5) An epoxy resin having a polybutadiene structure (DENALEX R-15EPT (trade name), the average degree of polymerization of the polybutadiene structure: 2 to 10, manufactured by Nagase ChemteX Corporation)

Epoxy Resin (b)
- (A-4) Bisphenol A diglycidyl ether ("jER828" (trade name) manufactured by Mitsubishi Chemical Corporation, the average degree of polymerization: 1.1 to 1.2)
- (A-6) Rubber-containing epoxy resin (BPA-328 (trade name), the average degree of polymerization: 1.3 to 1.4, manufactured by Nippon Shokubai Co., Ltd.)

Polyamine Compound (B)
- (B-1) 1,6-Hexanediamine (manufactured by Tokyo Chemical Industry Co., Ltd., active hydrogen equivalent: 29)
- (B-2) 1,12-Dodecanediamine (manufactured by Tokyo Chemical Industry Co., Ltd., active hydrogen equivalent: 50)
- (B-3) Trimethylhexamethylenediamine (manufactured by Tokyo Chemical Industry Co., Ltd., active hydrogen equivalent: 40)
- (B-4) 1,3-Cyclohexanediamine (manufactured by Tokyo Chemical Industry Co., Ltd., active hydrogen equivalent: 29)
- (B-5) 1,3-Bis(aminomethyl)cyclohexane (manufactured by Mitsubishi Gas Chemical Company, Inc., active hydrogen equivalent: 36)
- (B-6) Polyoxyalkylenediamine D400 (trade name, manufactured by Mitsui Fine Chemicals, Inc., active hydrogen equivalent: 100)
- (B-7) Polyoxyalkylenediamine T403 (trade name, manufactured by Mitsui Fine Chemicals, Inc., active hydrogen equivalent: 73)
- (B-8) 2-Methylpentamethylenediamine (manufactured by Tokyo Chemical Industry Co., Ltd., active hydrogen equivalent: 29)
- (B-9) m-Phenylenediamine (manufactured by Tokyo Chemical Industry Co., Ltd., active hydrogen equivalent: 27)
- (B-10) 4,4'-Ethylenedianiline (manufactured by Tokyo Chemical Industry Co., Ltd., active hydrogen equivalent: 53)
- (B-11) m-Xylylenediamine (manufactured by Tokyo Chemical Industry Co., Ltd.)

Other Compound (E)
- (E-1) Epoxysilane compound (KBM-403 (trade name), manufactured by Shin-Etsu Silicone)
- (E-2) Curing initiator (CI-2624 (trade name), manufactured by Nippon Soda Co., Ltd.)
- (E-3) 2-Ethyl-4-methylimidazole (manufactured by Tokyo Chemical Industry Co., Ltd.)
- (E-4) 3- or 4-Methyl-hexahydrophthalic anhydride (manufactured by Tokyo Chemical Industry Co., Ltd.)

As is clear from Table 1, Comparative Examples 1 and 2, in each of which bisphenol A diglycidyl ether having an average degree of polymerization of less than 2 was cured with a polyamine compound (B), were unacceptable in both elongation at break and sterilization resistance. Comparative Example 3, in which bisphenol A diglycidyl ether and a rubber-containing epoxy resin, each having an average degree of polymerization of less than 2, was cured with a polyamine compound (B) and other compounds, was also unacceptable in both elongation at break and sterilization resistance.

By contrast, Examples 1 to 20, in each of which an epoxy resin having an average degree of polymerization of 2 or more was cured, were acceptable both in elongation at break and sterilization resistance.

As is also clear from Table 2, by combining an epoxy resin having an average degree of polymerization of 2 or more with an epoxy resin having an average degree of polymerization of less than 2, elongation at break, breaking strength, and sterilization resistance can be improved in a well-balanced manner.

While the present invention has been described in connection with embodiments thereof, we do not intend to limit our invention in any detail of the description unless otherwise specified. Rather, the invention should be broadly construed without departing from the spirit and scope of the invention as defined by the appended claims.

REFERENCE SIGNS LIST

2 electronic endoscope (endoscope)
3 insertion section
   3a flexible tube
   3b angle portion
   3c tip portion
5 main-body operation section
6 universal cord
11 spiral tube
   11a metal strip
12 tubular net
13 cap
14 flexible tube substrate
   14a distal side
   14b proximal side
15 resin layer
16 coat layer
17 cured adhesive layer
31 illumination window
32 observation window
33 forceps port
34 nozzle
35 tip-portion main body
36 end cap
37 lens holder
38 prism
39 substrate
40 solid-state imaging element
41 cured adhesive
42 cured adhesive 43 observation unit
A air layer
L1 to L5 lens

What is claimed is:

1. A two-component adhesive for an endoscope, the adhesive comprising a base resin and a curing agent,
wherein the base resin contains an epoxy resin (A), and the epoxy resin (A) includes an epoxy resin (a) having an average degree of polymerization of 2 or more, and
wherein the curing agent includes a polyamine compound (B) represented by general formula (I):

General Formula (I)

in general formula (I), n represents an integer of 1 to 3, and $L^1$ represents a group with a valence of n+1 having an aliphatic hydrocarbon chain into which at least one oxygen is incorporated.

2. The adhesive for an endoscope according to claim 1, wherein the epoxy resin (a) is at least one of (a1) to (a4):
(a1) an epoxy resin having a polyester structure,
(a2) an epoxy resin having a polyurethane structure,
(a3) an epoxy resin having an acrylonitrile-derived constituent and a 1,3-butadiene-derived constituent, and
(a4) an epoxy resin having a polybutadiene structure.

3. The adhesive for an endoscope according to claim 1, wherein a content of the epoxy resin (a) in the epoxy resin (A) is 5 to 95 mass %.

4. The adhesive for an endoscope according to claim 1, wherein the adhesive is used in the form of a mixture of the base resin and the curing agent with the curing agent being present in an amount of 10 to 75 parts by mass based on 100 parts by mass of the base resin.

5. The adhesive for an endoscope according to claim 1, wherein the adhesive is used to fix a member in a tip portion of an insertion section of the endoscope.

6. The adhesive for an endoscope according to claim 1, wherein the adhesive is used to coat a string tightly bound around a connected portion of an insertion section of the endoscope.

7. The adhesive for an endoscope according to claim 1, wherein the adhesive is used to seal peripheries of an observation window and an illumination window in a tip portion of an insertion section of the endoscope.

8. The adhesive for an endoscope according to claim 1, wherein the adhesive is used to fix a prism in an optical device constituting the endoscope.

9. A cured product formed by curing the adhesive for an endoscope according to claim 1.

10. An endoscope comprising the cured product according to claim 9 and a member fixed with the cured product.

11. A method for producing an endoscope, the method comprising fixing a member by using the adhesive for an endoscope according to claim 1.

12. The adhesive for an endoscope according to claim 1, wherein the epoxy resin (a) is at least one of (a1), (a3) and (a4):
(a1) an epoxy resin having a polyester structure,
(a3) an epoxy resin having an acrylonitrile-derived constituent and a 1,3-butadiene-derived constituent, and
(a4) an epoxy resin having a polybutadiene structure.

* * * * *